United States Patent [19]

Greenfeld et al.

[11] Patent Number: 4,698,058
[45] Date of Patent: Oct. 6, 1987

[54] ULTRASONIC SELF-CLEANING CATHETER SYSTEM FOR INDWELLING DRAINS AND MEDICATION SUPPLY

[75] Inventors: Albert R. Greenfeld, 31430 Glenbridge Rd., Westlake Village, Calif. 91361; Herbert Reis; Bernhard R. Tittmann, both of Thousand Oaks, Calif.

[73] Assignee: Albert R. Greenfeld, Westlake Village, Calif.

[21] Appl. No.: 787,728

[22] Filed: Oct. 15, 1985

[51] Int. Cl.⁴ .............................................. A61M 25/00
[52] U.S. Cl. ...................................... 604/266; 604/22; 128/24 A; 128/328
[58] Field of Search ............... 604/266, 22, 267, 327; 128/24 A, 328, 660, 739, 24 A

[56] References Cited

U.S. PATENT DOCUMENTS

| | | | |
|---|---|---|---|
| 3,830,240 | 8/1974 | Antonevich et al. | 128/328 |
| 3,896,811 | 7/1975 | Storz | 128/24 A |
| 3,941,122 | 3/1976 | Jones | 128/24 A |
| 4,030,505 | 6/1977 | Tessler | 128/24 A |
| 4,136,700 | 1/1979 | Broadwin et al. | 128/24 A |
| 4,192,294 | 3/1980 | Vasilevsky et al. | 128/1 R |
| 4,474,180 | 10/1984 | Angulo | 128/24 A |
| 4,509,947 | 4/1985 | Lattin | 604/266 |
| 4,516,398 | 5/1985 | Wuchimich | 128/24 A |

Primary Examiner—Stephen C. Pellegrino
Assistant Examiner—John D. Ferros
Attorney, Agent, or Firm—Romney Golant Martin Sheldon & Ashen

[57] ABSTRACT

Vibration is conveyed to the proximal orifices of an indwelling catheter to disintegrate accumulated clogging deposits, large suspended particles and contaminating bacteria, viruses, fungi, etc. Orifices may be recessed, hooded or enclosed, and in some cases the catheter tip should be of absorptive material, to deter propagation of the vibration to the parts of the patient's body outside the catheter. Vibration may be conveyed to the orifices by (1) a solid fiber embedded in the catheter walls or positioned in an auxiliary lumen of the catheter; or (2) by a liquid in an auxiliary lumen—which may be formed as an annular space surrounding the main lumen. Preferably the apparatus measures the amount of vibration absorbed by the deposits or bacteria, etc., as a function of frequency, and automatically concentrates the vibration at frequencies where absorption is particularly high, to maximize the disintegration of deposits, particles, bacteria or other bioactive objects. Ultrasonic shear waves are thought more effective than compressional waves, but both may be used.

25 Claims, 15 Drawing Figures

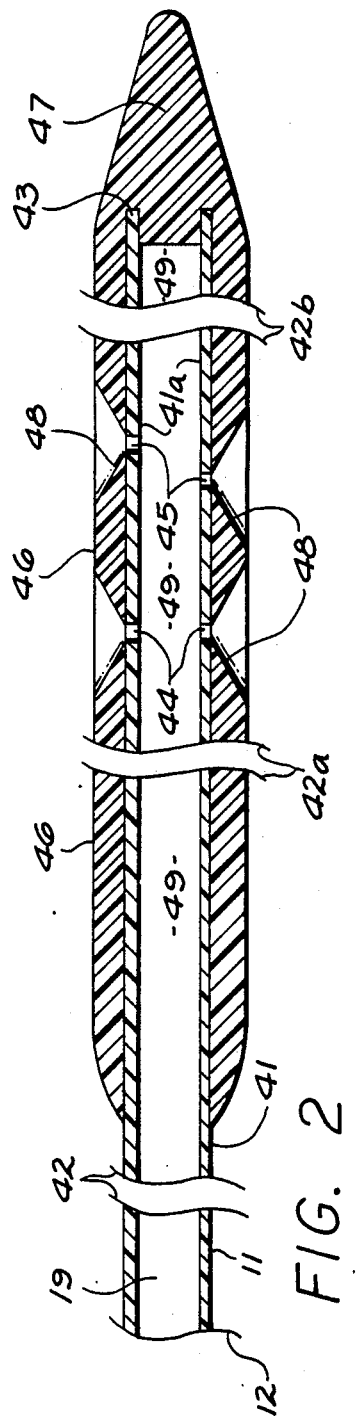
FIG. 2
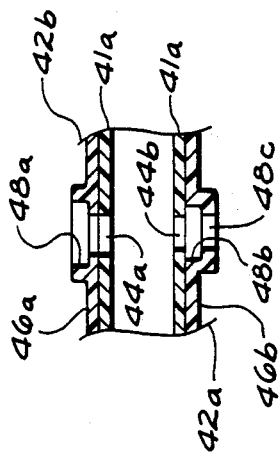
FIG. 3
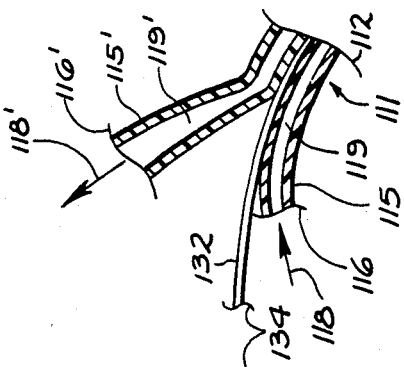
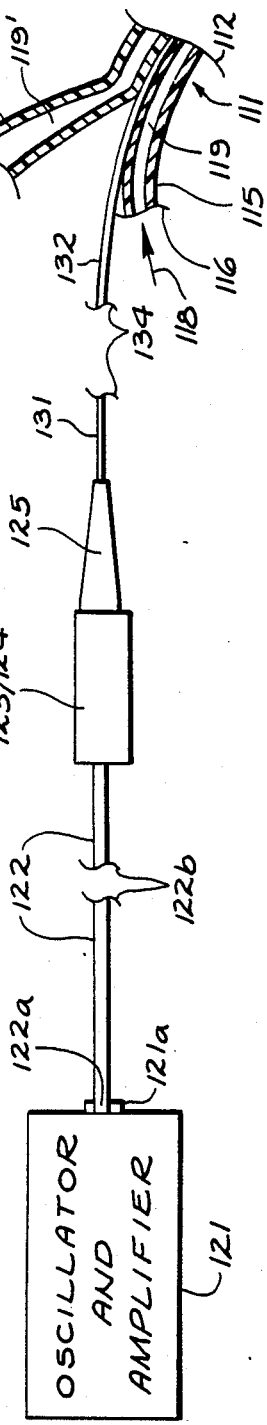
FIG. 4

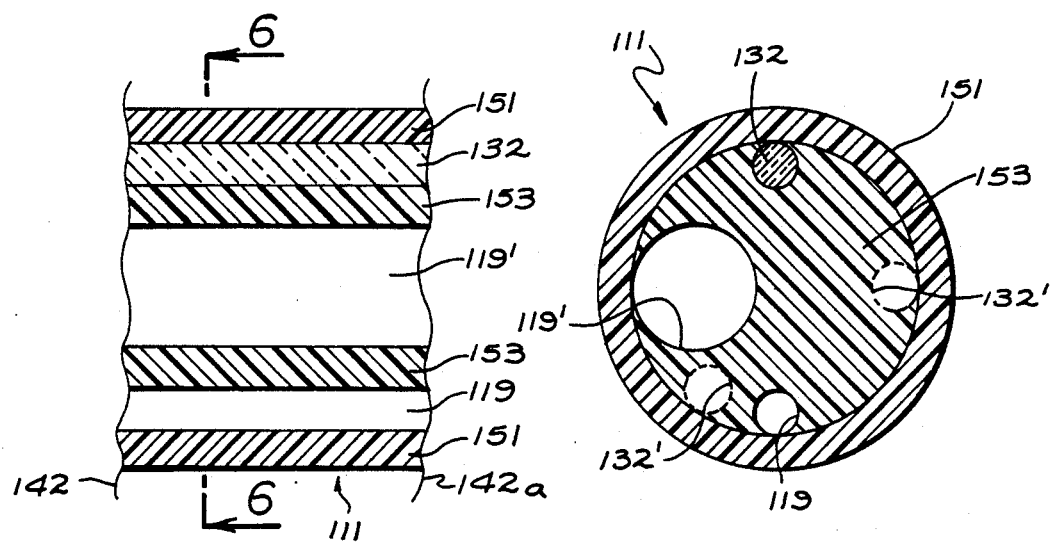
FIG. 5
FIG. 6
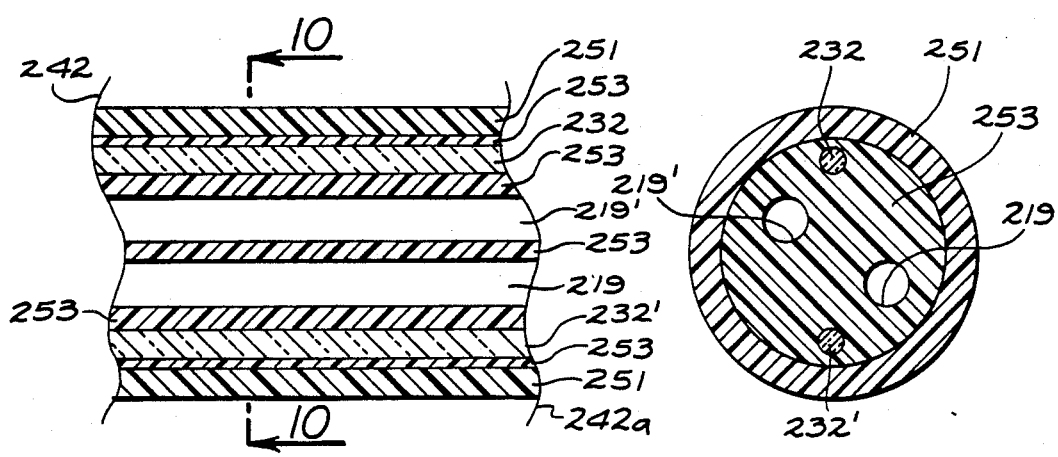
FIG. 9
FIG. 10
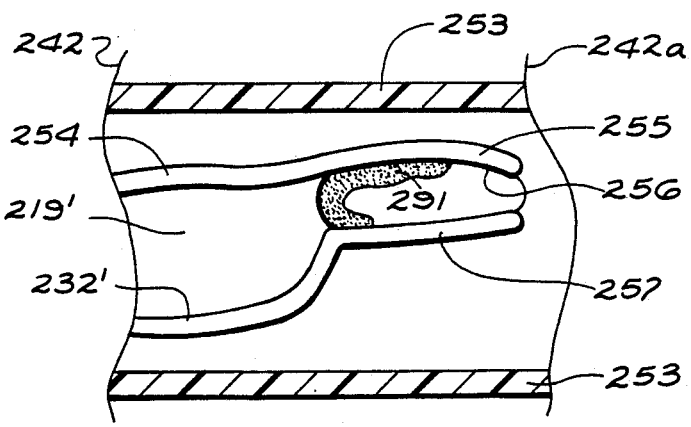
FIG. 11

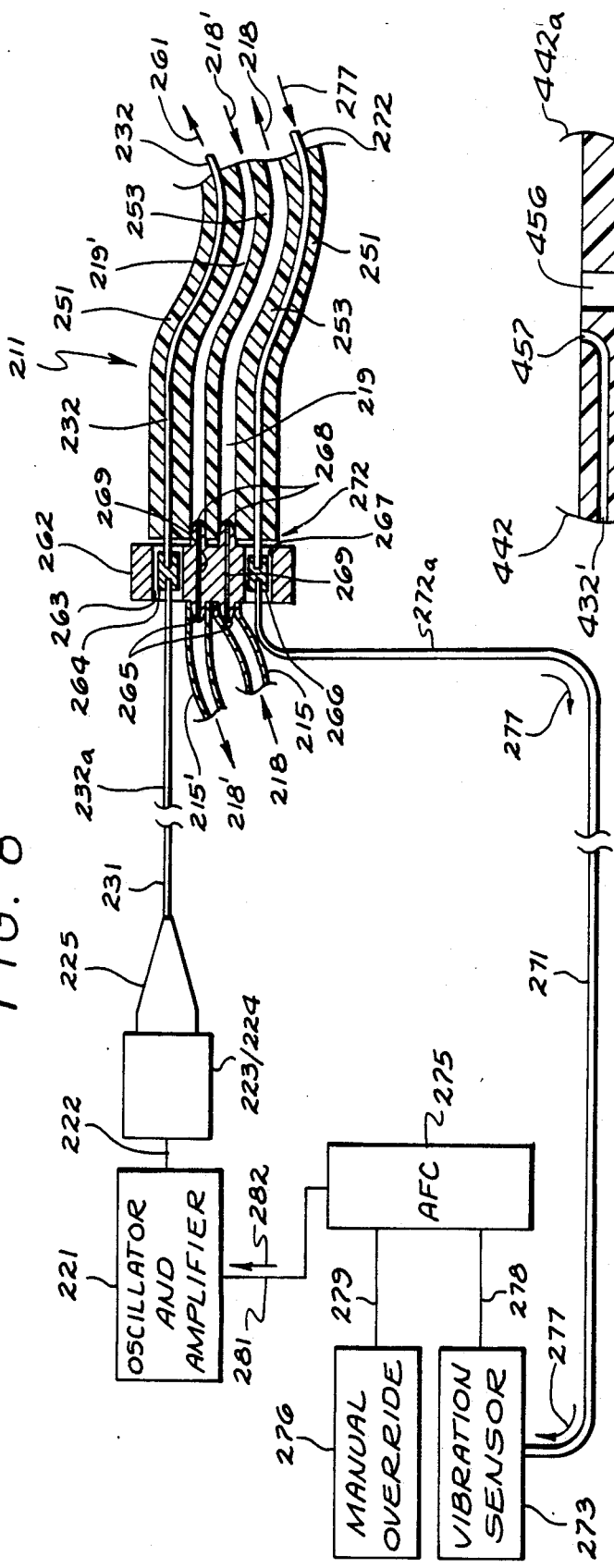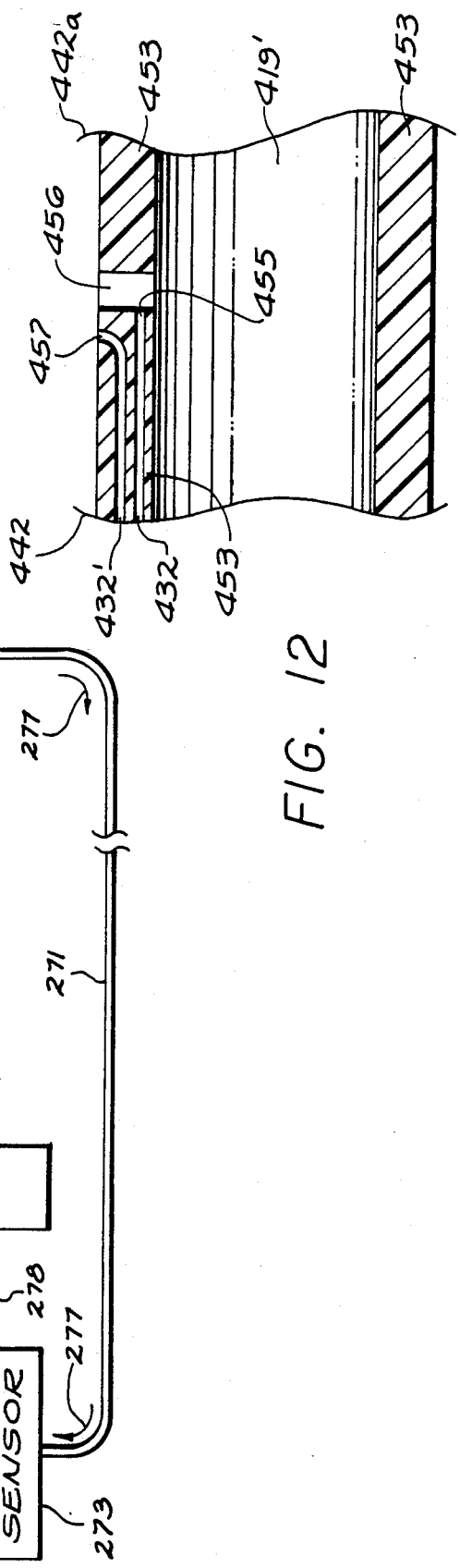

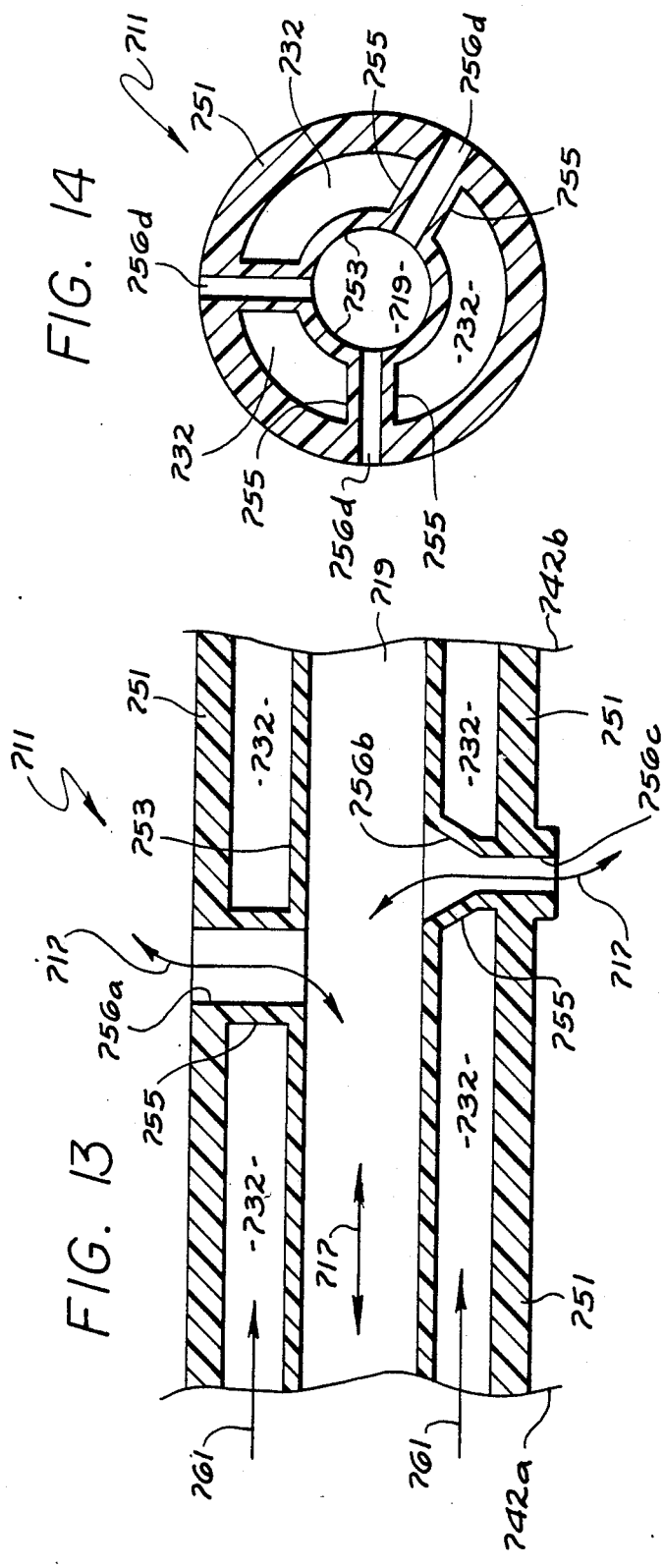
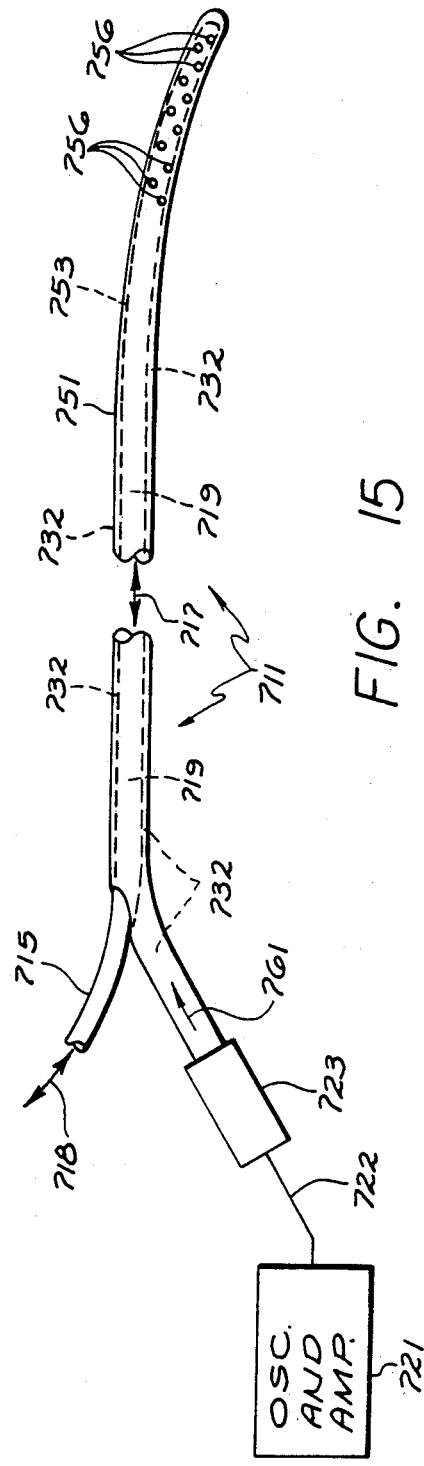

ULTRASONIC SELF-CLEANING CATHETER SYSTEM FOR INDWELLING DRAINS AND MEDICATION SUPPLY

BACKGROUND

1. FIELD OF THE INVENTION

This invention relates generally to indwelling catheters, and more particularly to systems for keeping the proximal orifices of such catheters free of clogging deposits, large suspended particles, and contaminating bacteria. Such catheters are used in medical procedures for both humans and animals.

(An "indwelling" catheter is one that is emplaced and left in place for protracted periods, such as fifteen minutes or longer. It has been known to leave catheters in place for more than two years. In this document the word "proximal" is used with respect to the patient's body, not with respect to the instrumentation at the other end of the catheter. The word "medical" is used to encompass surgical as well as medicinal therapies. The word "bacteria" is used to encompass bacteria, viruses, fungi, and other bioactive materials.)

2. PRIOR ART

Indwelling catheters are well known, both for supplying medication and nutriments—as, for instance, in intravenous tubes—and for draining urine, exudates or other fluids from a patient's body. A major problem in the protracted use of such catheters arises from clogging or contamination of their channels and proximal orifices, and from large particles suspended in the fluids.

This problem is more crucial in drains, since the conditions that give rise to the drainage requirement in the first place are generally the same conditions that produce undesirable substances such as congealing mucus, pus, and sometimes even particulate organic debris.

Of course clogging of an indwelling drain is a serious matter since the drainage required by the patient's condition is thereby defeated. These undesirable substances, however, not only mechanically obstruct the orifices but also carry bacteria, which often lodge in stagnant regions at the orifices. Such an accumulation of bacteria is a breeding site for disease germs that may not even be active in the patient to begin with, and thus creates a serious risk of secondary infection and severe complications.

Supply tubes such as intravenous catheters are also subject to contamination by bacteria already within the patient's body or introduced by external contamination, and to a lesser extent are subject to clogging. Supply catheters that carry nutriments are an attractive site for accumulation of bacteria that divert the nutriment supply. In this way a dual negative effect is generated: the nutriment needed by the patient is at least partially withdrawn, and the patient's condition may be threatened by the bioaction of the bacteria.

In the case of catheters that deliver medication, bacteria threaten the integrity of the medical bioactivity in totally unpredictable ways. Bacteria can impair or completely metabolize the medicine or can even amplify its action—as by stripping away moderating molecular groups or excipients.

Regular cleaning is accordingly an essential part of any therapy that requires indwelling catheterization. Unfortunately, however, the usual procedure for cleaning a catheter entails removal from the patient. Sometimes such a catheter is replaced by a clean unit and taken away for cleaning elsewhere, and sometimes it is forthwith cleaned and put back into the patient's body.

In either case, the likelihood of trauma to the patient is substantial. The opportunity for aggravation of the foregoing problems by inadequate cleaning is likewise substantial.

Patients are known to develop several kinds of undesirable reactions to repeated removal and replacement of catheters. Repetitive insertion of intravenous tubes, for example, badly irritates and scars the areas where the needles are emplaced—sometimes so seriously that the intravenous supply must be moved to an entirely different part of the body. Patient morale correspondingly suffers, often enough to cause significant depression and psychosomatically induced deterioration of the patient's physical condition. Furthermore, each removal and replacement increases the chance of bacterial contamination and blood clots, which clog or can add to the infection, or both.

When incompletely cleaned catheters are placed in a patient's body, the result can be disastrous. Infection that may have been localized in the area of the proximal orifices of the catheter can spread throughout the entire route of the catheter passage. When an incompletely cleaned catheter taken from one patient is emplaced in a different patient, the spread of local infection and even fatal disease assumes catastrophic character.

Although the present state of the art in catheter cleaning is not really effective at all against bacterial accumulations, it should be understood that even far more effective techniques would be hard put to completely eliminate bacterial attack. The reason is that bacteria actually have a mechanism for surviving (as a group) cleaning techniques. In particular, bacteria mutate rapidly and thereby avoid the effects of almost any adverse condition that can be pragmatically imposed upon them. Thus some bacteria are found alive and well in permafrost, while others survive temperatures over 3000° F. and some have been found doing nicely in lava flows. Some of these bacteria metabolize sulfur compounds; hence it may be appreciated that mere chemical agents—at least those that are in the least compatible with the survival of the patient—are hopelessly inadequate over any protracted treatment period.

All of these conditions are aggravated by mechanical stress, not only at the surface of the patient's body but at every point where the catheter is subject to flexure during emplacement or during the patient's necessary daily activities.

Foregoing references to incomplete cleaning of indwelling catheters, tragically enough, are far from academic. It is well documented, though ironic, that in this era of advanced scientific sophistication the most basic sanitation procedures are more honored in the breach than in the observance, at many major medical facilities.

Based upon a recent public-health survey it has been asserted that a significant percentage of all hospitalized patients contract an infection while in the hospital. The percentage is even higher (reportedly much higher) in such vital areas as intensive-care units. Whether due to economics, faulty management or societal degradation—all of which causes have been invoked in the commentary—this phenomenon poses a monumental threat to the effectiveness of institutional therapies.

Earlier efforts to avoid the customary steps of manual withdrawal, cleaning and reemplacement have been ineffectual, impractical or at least too cumbersome to gain general acceptance.

The state of the art for in situ cleaning, with respect to actual widespread usage in medical facilities, is simply irrigation of the catheter with any of a great variety of supposedly cleansing solutions. Such irrigation is not done by machinery but simply by hand, using a syringe. Typical of this approach is U.S. Pat. No. 4,296,747 to Ogle, describing an improved device for introducing cleansing or irrigating fluid into a Foley catheter—a catheter assembly that is used to drain urine from the bladder.

Irrigation techniques, while generally practical, are not adequately effective. Other systems tend toward the converse: for example, U.S. Pat. No. 3,416,532 to Grossman discloses a self-scraping drainage catheter formed of inner and outer tubes. The outer tube defines numerous orifices near its proximal end, and the inner tube has a slanted sharp edge near its proximal end. When the orifices become clogged, the inner tube may be reciprocated so that the slanted edge tends to scrape off clots or other clogging of the perforations in the outer tube.

Though elaborate and awkward to use, this system is probably helpful in removing debris that extends through the perforations into the space within the outer tube. Such a system, however, does little to clean away accumulated substances that are actually within the orifices themselves and do *not* extend into the inner tube, or accumulations that are just outside the catheter in the patient's body.

Other patents which teach systems for unclogging catheter perforations include U.S. Pat. Nos. 3,863,641 to Popa, 2,642,873 to Rice, 4,228,802 to Trott, 3,601,128 to Hakim, and 3,955,574 to Rubinstein.

Popa describes a dual-catheter thoracic aspiration drain used especially after heart surgery or after a traumatism in the thorax. In this device an inner catheter ends in a balloon that can be inflated to seal against the internal surface of the outer catheter. While thus sealed the balloon is drawn outwardly, creating a suction that forcibly pulls debris into the inner tube, whence it is more readily drawn out by the aspirator. This system plainly relies upon well-trained personnel for vigilant monitoring and manipulation.

Rice's invention is similar to Grossman's, but in Rice the inner tube has orifices aligned with those in the outer tube, and is rotated rather than reciprocated. Trott's proposed catheter likewise would have a "detachable auger assembly" and a "mechanical expanding device" for breaking up clots and debris at the proximal entrance to the catheter, and also includes an annular lumen for introduction of irrigating fluid.

Hakim describes a "ventriculoatrial shunt"—a device for draining cerebrospinal fluid into the venous blood system to relieve hydrocephalus. In this system, clogging of the cerebroventricular catheter by the choroid plexus or by other matter is discouraged by a sort of backflushing technique. A portion of the cerebrospinal fluid is valved to cyclically flow back into the cerebral ventricle. This technique is highly specialized to situations in which the primary danger is of clogging by material of a fibrous character, and also appears sufficiently fussy as to require knowledgeable and virtually constant monitoring. Such an approach is undoubtedly justified in critical circumstances such as brain trauma, but would be difficult or impractical to sustain in less acute cases.

Rubinstein too discloses a cyclical alternation of vacuum and pressure applied to a catheter drain, so that suction is periodically interrupted by predetermined periods of blowing, to help keep the proximal entrances clear.

As stated earlier, all these known systems either are impractical for general use or are simply ineffective for protracted catheterization.

In another area, it is known to use vibration for clearing obstructions from certain internal passageways and cavities of a patient's body. U.S. Pat No. 3,352,303 to Delaney reveals an ultrasonic vibratory system for "lysis of blood clots" in veins and arteries. U.S. Pat. No. 3,433,226 to Boyd describes a similar system for "decimation of atheromatous plaques"—i.e., of fatty degenerations of the arterial lining.

U.S. Pat. No. 3,861,391 to Antonevich and Goodfriend provides for ultrasonic "disintegration of urinary calculi." This theme is elaborated by U.S. Pat. Nos. 3,927,675 to Pohlman and 4,192,294 to Vasilevsky et al.; and expanded by Tessler in U.S. Pat. No. 4,030,1505 to encompass disintegration of kidney and bladder stones.

Some Russian workers have reported efforts to destroy bacteria using ultrasonic vibrations. These efforts, however, have not been directed to cleansing of catheters or even to channeling of such vibrations into sites within a patient's body. Furthermore they have not addressed the difficult mutational-escape problem discussed above.

The prior art thus deals to some extent with ultrasound as a means for removal of preexisting deposits such as blood clots, arterial plaque, and urinary-tract stones through working catheters briefly inserted for the purpose. It does not, however, teach or even suggest that ultrasound could be used to maintain free flow and sanitation of a catheter itself, or in particular of an indwelling catheter.

Of less interest are ultrasonic catheter devices for determining the location of objects within a patient's body. For example Colley, in U.S. Pat. Nos. 4,354,500 through 4,354,502, proposes to find air emboli using such devices; and Kubota, in U.S. Pat. Nos. 4,344,436 and 4,346,702, describes how to use such devices to find the location of a catheter tip relative to the patient's body.

BRIEF SUMMARY OF THE DISCLOSURE

Our invention provides a self-cleaning catheter system, for use in protracted transfer of fluid—in either direction—between a patient's body and a point outside the patient's body. Our invention is primarily directed to medical procedures for humans, but is also valuable in veterinary applications.

This invention requires virtually no monitoring or sophisticated manipulation. It is simply used by medical personnel in the normal fashion of conventional catheters, except that it also must be plugged in or turned on and off, and like other apparatus it should be periodically serviced.

The invention includes a catheter, and at least one orifice that is defined near the proximal end of the catheter and that is subject to the presence of undesirable substance during the fluid transfer. By "catheter" we mean an artificially created channel which leads to and enters a mammalian body. Various kinds of undesirable substance have been identified in the preceding section of this document.

The invention also includes a source of mechanical vibration. In addition, the invention includes some means for conveying the vibration from the source to the catheter orifice, to disintegrate the undesirable substance and maintain the protracted fluid transfer relatively free from obstruction and contamination by the undesirable substance. In this document for purposes of generality this last-mentioned element of our invention will be called the "vibration-conveying means."

Preferred embodiments of our invention also include some means for deterring propagation of the vibration into the parts of the patient's body outside the catheter—in other words, for protecting the patient from escape of the vibration through the wall or orifice of the catheter. In many circumstances, serious harm to body tissues such as blood vessels, nerves and solid organs can occur if such protection is not provided.

The vibration-conveying means advantageously include a solid fiber in the catheter, to conduct the vibration directly to the orifice. For example, the fiber may be embedded in the catheter wall; alternatively the fiber may be carried within an auxiliary lumen of the catheter. If there is more than one orifice, there may be accordingly more than one fiber.

Yet again, the vibration-conveying means may include a liquid constrained within an auxiliary lumen of the catheter. In this case, the catheter further includes some structure preventing fluid communication between the auxiliary lumen and the orifice. The auxiliary lumen may be annular, surrounding the main fluid-transfer lumen of the catheter; if so, the orifice must pass through the walls of both the inner main lumen and the outer annular lumen, and the fluid-commmunication-preventing structure is essentially a wall of the orifice. This configuration may be particularly advantageous if there are many orifices, since the fluid in the annular lumen thereby brings the vibration into effective contact with the wall of each orifice.

Our invention also preferably includes some means for measuring the absorption of the vibration by the undesirable substance. If the vibration-conveying means include a solid fiber as previously mentioned, the measuring means may include a second solid fiber in the catheter; this second fiber is positioned to receive vibration that is not absorbed by the undesirable substance. The second fiber transmits such unabsorbed vibration back through the catheter and out of the patient's body to a detection device. Such measurement can be calibrated to provide an indication of the amount of vibrational energy consumed in disintegrating the substance, and thus an estimate of the amount of substance disintegrated.

The operating parameters of the vibration source—in particular the vibrational frequency or frequencies employed—may then be selected to maximize the effectiveness of the apparatus in disintegrating the undesirable substance. Hence the invention preferably also includes some means for adjusting the frequency (and other characteristics, if desired) of the vibration.

Advantageously the adjusting means are automatically responsive to the measuring means to maximize the absorption of the vibration by the substance. Since there are likely to be several different substance structures present, the invention preferably is capable of directing vibration at a computer-controlled plurality of frequencies—either simultaneously or in a repeating frequency-sweep sequence—to each orifice. If automatically responsive to the measuring means, the adjusting means preferably select a plurality of frequencies exhibiting relatively high values of absorption, for conveyance to each orifice.

By using such constantly shifting resonances, our invention provides a bactericidal technique that can actually follow the bacteria as they *mutate!* Although many known bacterial behaviors defy belief, it is difficult to hypothesize any mutational mode (or resultant vibration-resistant bacterial structure) that could escape this cleaning technique.

We believe that for the purposes of our invention the most effective vibration is at ultrasonic frequencies and propagates as shear waves, rather than longitudinal or compressive waves; however, we believe that the use of any such vibrations is within the scope of our invention.

Thus our invention will break down particles of undesirable substance without harming the host—i.e., the patient's body. The invention facilitates fluid flow, either continuous or pulsed flow as may be preferred, through the catheter tube. It inactivates or destroys any infectious agents such as bacteria at the proximal orifices of the tube—again without harming the host.

Our invention contemplates using vibration measurements not only to monitor the amount of vibrational energy consumed in contaminant disintegration as discussed in the preceding paragraphs, but also to monitor the amount of vibration leakage into the host's surrounding tissues. As will be seen, leakage monitoring can be combined with generation of an alarm signal for medical personnel, or with automatic control of the vibration apparatus.

All of the foregoing operational principles and advantages of the present invention will be more fully appreciated upon consideration of the following detailed description, with reference to the appended drawings, of which:

BRIEF DESCRIPTION OF THE DRAWINGS

FIG. 2 is a longitudinal section of the proximal end of a catheter that may form a part of the FIG. 1 embodiment.

FIG. 3 is a longitudinal section of a portion of a catheter that may be used as an alternative to the catheter of FIG. 2.

FIG. 4 is a partially schematic and partially elevational view, similar to FIG. 1, of another embodiment of our invention. In this view too a portion of the elevation is shown in longitudinal section.

FIG. 5 is an enlarged longitudinal section of a short piece of the catheter of the FIG. 4 embodiment, taken at a point generally intermediate to the proximal and distal ends of the catheter.

FIG. 6 is a cross-section of the catheter of the FIG. 4 embodiment, taken along the line 6—6 of FIG. 5.

FIG. 8 is a compound view similar to that of FIGS. 1 and 4, but representing yet another embodiment of our invention.

FIG. 9 is a longitudinal section, similar to FIG. 5, of a short length of a catheter suited for use in the FIG. 8 embodiment.

FIG. 10 is a cross section of the catheter of the FIG. 8 embodiment, taken along the line 10—10 of FIG. 9.

FIG. 11 is an enlarged longitudinal section similar to FIG. 7, but taken at the proximal end of the FIG. 8 catheter.

FIG. 12 is also an enlarged longitudinal section, at the proximal end of a variant form of our invention, showing radial relative placement of transmitting and receiving fibers to permit monitoring of leakage vibration.

FIG. 13 is a longitudinal section, analogous to those of FIGS. 5 and 9, of a catheter that can be used in yet another embodiment of our invention.

FIG. 14 is a cross section of the FIG. 13 catheter, but taken at a point along the catheter that does not appear in FIG. 13.

FIG. 15 is a generally schematic view of the FIG. 13 catheter in use.

DETAILED DESCRIPTION OF PREFERRED EMBODIMENTS

Figure 1:
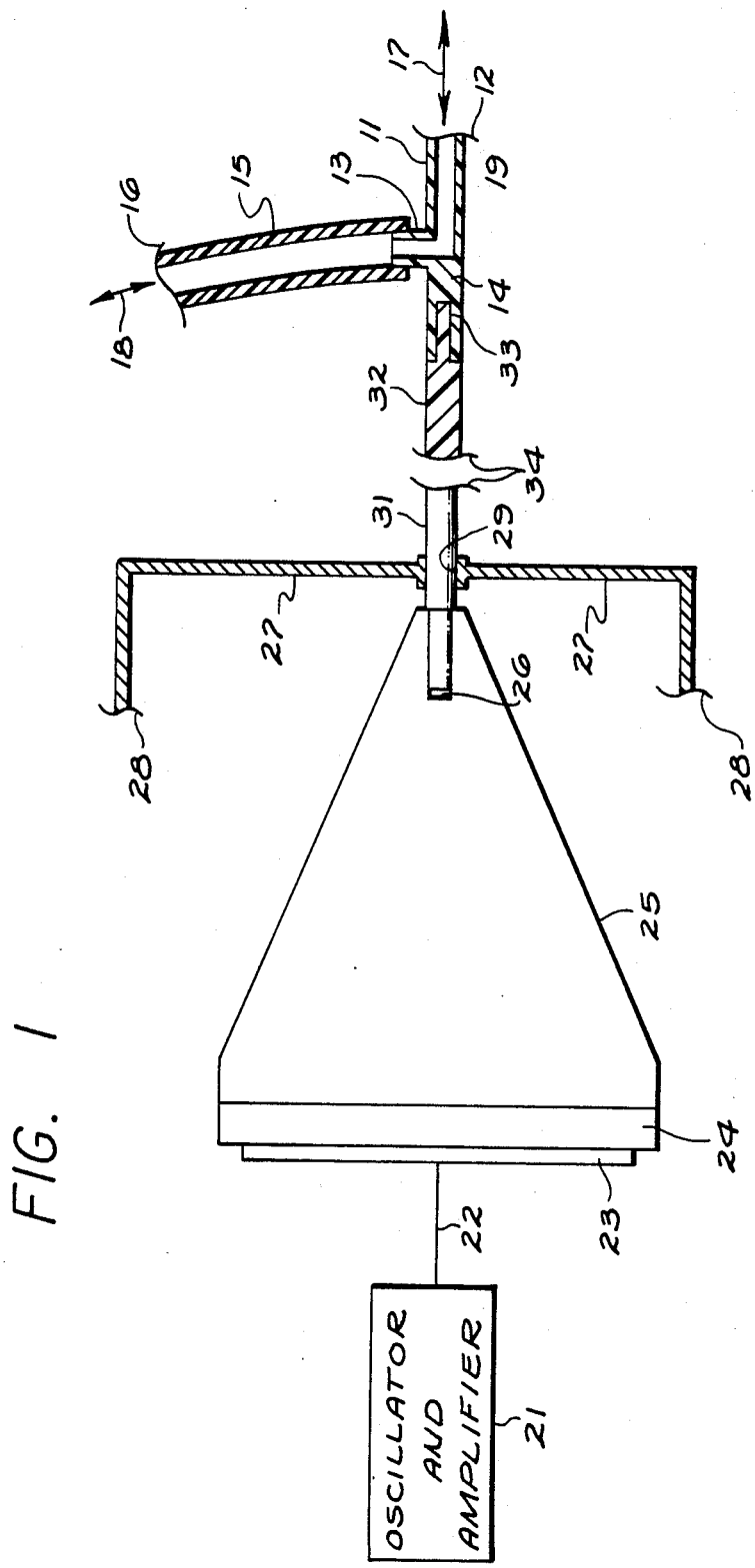
FIG. 1 is a partially schematic and partially elevational view of one particularly simple embodiment of our invention. A portion of the elevational view is shown in longitudinal section.

As shown in FIG. 1, the invention includes a catheter 11 that defines a passageway 19 for flow of fluids —liquids, gases, or both. Such fluids flow into or out of the body of a patient, as suggested by the bidirectional arrow at 17. It will be understood that the portion 11 of the catheter appearing in FIG. 1 is distal with respect to the patient's body. For purposes of illustrating the portion of the invention that is outside the patient's body, the illustration of the catheter is interrupted at 12.

The distal portion 11 of the catheter has a hose fitting 13 for attachment of a supply or drain tube 15, which similarly defines a flow path as suggested by the arrow at 18 between the passageway 19 and a source of—or a drain for—the fluids of interest. As such sources and drains are well known in the art, neither is illustrated, the drawing of the supply or drain tube 15 being simply interrupted at 16.

The embodiment of FIG. 1 further includes a special vibration-transmitting fitting 14. This fitting 14 may be integral with the catheter 11 and aligned with the body of the catheter 11 as shown, while the fluid supply or drain tube 15 is disposed at an angle to both. In this way the vibration-transmitting fitting 14 can project vibration axially into the material of the catheter wall 11 and into the passageway 19, from a source to be described. For some applications the fitting 14 need not be integral with, but may instead be attached to, the catheter 11—as will be clear from the following discussion.

The FIG. 1 embodiment of our invention also has vibration source and transmission devices. These include a frequency-controllable electrical oscillator and amplifier 21, electrical leads 22 conveying amplified electrical oscillations or to a piezoelectric or other transducer 23, a vibration receiver/transmitter plate 24 firmly secured to the transducer, a solid horn 25 firmly secured to or integral with the plate 24, an attachment receptacle 26 formed in the end of the horn 25 opposite the plate 24, and a solid rod 31-32-33 for transmitting vibration from the horn 25 to the previously mentioned fitting 14. This is only one of various possible ways of energizing the apparatus.

Electrical oscillations in the leads 22 cause the transducer 23 to vibrate mechanically, generally at a frequency that is directly related to the frequency of the electrical oscillations. This mechanical vibration of the transducer 23 is coupled to the plate 24, which may to some degree inertially smooth out the behavior of the transducer 23 to provide a "cleaner" vibration for use in the catheter. Vibration in the plate is in turn coupled to the horn 25, which by virtue of its tapered construction concentrates the vibration into the relatively small cross-sectional area of the receptacle 26. The concentrated vibration proceeds into the rod 31-32-33. For practical purposes the source components 21, 22, 23, 24, 25 and 26, and the distal part 31 of the rod 31-32-33 when in use, may be housed in a suitable enclosure 27—shown interrupted at 28 for convenience of illustration. The enclosure 27 advantageously has an aperture 29 for passage of the rod 31 into the receptacle 26. Electrical power may be supplied through the enclosure 27 to the oscillator and amplifier 21 by a conventional power connection (not illustrated).

The proximal portion 32-33 of the transmitting rod 31-32-33 is configured to firmly mate with and engage the transmitting fitting 14, as illustrated by the male-female interconnection in the drawing. The male and female portions 33 and 14 of the engagement are advantageously threaded together or otherwise fastened, to secure the engagement against separation during transmission of mechanical vibration from the source components into the catheter 11.

The vibration-transmitting distal portion 31 of the rod 31-32-33 is advantageously continuous with the proximal portion 32-33, the illustrated gap at 34 being merely for purposes of suggesting an intervening rod length of indefinite extent. As stated earlier, the source components 21 through 27 may be separated from the catheter 11 at the patient's bedside by many rooms, and may even be on separate floors, in a medical facility with centralized source components; or alternatively the source components 21 through 27 may be disposed at the immediate site of use. If the distance is relatively long, the material and the configuration of the rod 31-32 are preferably chosen for minimal attenuation per unit length of the rod 31-32, so that effective amplitude remains at the fitting 14 for cleaning action within the catheter 11. Alternatively, or in addition, a booster/repeater can be used.

If the fluids to be passed through the catheter are liquids, then they may be the primary medium for transmission of vibration along the catheter 11 from the transmitting fitting 14. If the fluids of interest are gaseous, then they may not be capable of supporting sufficient power transmission for effective cleaning action. In that case, either the material and structure of the catheter wall 11 must be selected for suitable vibration-transmitting properties or one of the other forms of our invention must be employed.

The catheter distal portion 11 of FIG. 1 may be continued as illustrated in FIG. 2 into a distal portion 11, intermediate portion 41, and proximal portions 41a and 43. As will be clear from the reference numerals 12 in FIGS. 1 and 2, the portion 11 of FIG. 1 is continuous with the distal portion 11 of FIG. 2. An interruption of essentially indefinite length is shown at 42, followed by the proximal portion 41-43 of the catheter. It is this latter portion that passes within the body of the patient, defining a passageway 49 that communicates with the passageway 19 of the distal portion 11.

The proximal portion 41-43 of the catheter may have a sheath 46 that absorbs vibration—to prevent harmful radial propagation of vibration into the patient's tissues surrounding the catheter. The sheath 46 may be continued into an elongated tip 47, to similarly prevent harmful axial propagation of vibration from the proximal end of the catheter. In this way the patient may be protected from the vibration projected into the catheter 11-41-43 by the fitting 14 (FIG. 1). If the fluids to be passed through the catheter are gases, the walls 11-41-41a-43 of the catheter may be made of vibration-transmitting material.

In order to function as a catheter, the tube 11-41-41a-43 must have some proximal opening or openings for inward or outward flow of fluid. For some purposes there may be a single axial opening at the very proximal tip of the catheter, but the form of the invention shown in FIG. 2 has a multiplicity of radial orifices 44, 45. These orifices may be axially aligned in sets as at 44, or may be offset as at 45. (It will be understood that in any given catheter for particular applications, either all the orifices may be axially aligned as at 44, or all may be offset as at 45. For still other purposes it may be preferred to have some orifices aligned and some offset.)

In any event it is this orifice or these orifices of the catheter that tend to be clogged and to produce bacterial accumulations. Accordingly, whether by transmission via liquids within the passageway 19-49 or via the wall material 11-41-41-a, the mechanical vibration is conveyed to the orifice or orifices 44, 45. At these points the vibration tends to continuously interfere with both formation and maintenance of deposits. The vibration thus tends to continuously keep undesirable substances in suspension so that they are swept through and past the orifices in whichever direction the fluid is flowing.

The sheath 46 may be cut away as in generally conical configurations at 48 to minimize any tendency of the sheath to support accretion of undesirable substances where the vibrational energy density is greatly reduced just outside the orifices 44, 45. It is also important, however, to avoid excessive leakage of the vibration into the patient's body at these very points. The best configuration of the radially outward portions of the catheter wall 41a and of the sheath 46 adjacent the orifices 44, 45 thus will depend upon the balance between avoiding excessive accumulation of undesirable substances and avoiding excessive vibration leakage. This tradeoff may be effectuated in a straightforward fashion in light of the principles described in this document, and based on collection of operational data from prototypes in ordinary ways. This tradeoff will vary strongly with proximity of the catheter to various types of tissues in the body.

The amount of vibrational energy that is required —and the amount that is permitted—at the orifices 44, 45 of the catheter wall proper 41a will vary with several factors, such as the type of fluid that is to flow through the catheter, the type of body tissue which surrounds the intermediate portion 41 of the catheter, the portion of the patient's body into which the proximal part of the catheter extends, and perhaps most importantly the types and severity of undesirable substance that may be anticipated. These same factors accordingly must guide the routine design of apparatus according to our invention, to effectuate the tradeoff discussed above.

In situations requiring higher energy density, for example, the conical contours 48 of FIG. 2 may be replaced by other configurations such as suggested in FIG. 3. (It will be understood that in a typical circumstance either the configuration 48a or the configuration 48b-48c may be used, rather than both in a single catheter.) One configuration appropriate for intermediate-to-high energy, or intermediate-to-high danger from vibration leakage, may be a raised crater-like guard rim 48a, formed in the sheath 46a surrounding each orifice 44a, but spaced radially (relative to the axis of the orifice) outward.

For higher energy, or higher danger from leakage, an appropriate configuration may be a secondary aperture 48c that is formed in the sheath 46b and that defines with the wall 41a disc-shaped trap chamber 48b. This trap chamber 48b may be sized in diameter or depth to resonate at a nominal center frequency of the mechanical vibration—or, alternatively, the vibration can be periodically adjusted to a frequency at which the chamber 48b resonates —to help keep the structure 48b-48c free of obstructions while minimizing radiation at the secondary aperture 48c.

Precise proportions and contours of the raised guard 48a or trap 48b-48c, relative to the diameter of the catheter wall 41a and the sheath 46a proper, will also depend upon the particular application for which a catheter is intended. In some cases a sheath 46 may be unnecessary, but guards 48a or traps 48b-48c may be formed integrally with or attached individually to the catheter wall 41a proper adjacent to each orifice or adjacent to particular orifices where radiation is of particular concern.

The foregoing discussion of the fairly simple embodiment of FIGS. 1 through 3 will be understood to apply equally to the discussion of other embodiments that follows below, particularly with regard to the principle of sheathing as appropriate and with regard to the principle of providing various forms of conical contour, or guard or trap, at the orifices.

FIG. 4 shows a preferred embodiment of our invention that has a catheter with separate supply and drain tubes 115, 115', and that uses a solid fiber 132 for transmitting vibration to the proximal orifices of the catheter. The source components 121 through 131 are essentially the same as the correspondingly numbered elements in FIG. 1, except that in FIG. 4 the prefix "1" has been inserted before each reference numeral; and except that in FIG. 4 the electrical leads 122 are shown as being of indefinite length and having a repetitively removable plug 122a that mates with a receptacle 121a at the output of the oscillator and amplifier 121.

Thus the source components of FIG. 4 may be conceptualized either as (1) a central oscillator and amplifier 121, with electrical transmission lines 122 running to individual transducers 123/124 at the patient's location—or (2) a central oscillator, amplifier and transducer 121-124, with mechanical vibration transmission lines 131-132 running to individual catheters at the patient's location, more in the fashion of FIG. 1. The same alternatives are available with respect to the FIG. 1 embodiment.

As in FIG. 1, the FIG. 4 embodiment is shown with the catheter 111 truncated at 112, and the input tube 115 and output tube 115' are likewise truncated at 116 and 116' respectively. Fluids such as air or other gases, or liquids, or both, may flow into the patient's body, as indicated by flow arrow 118, through a passageway 119 defined in the input tube 115; and may flow out of the patient's body, as indicated by arrow 118', through a passageway 119' defined in the output tube 115'. The vibration produced in the transducer 123/124 is concentrated at 125 and then conducted by a plastic, glass, or quartz fiber 132 to the proximal orifices of the catheter 111.

FIGS. 5 and 6 show the intermediate portions of the FIG. 4 catheter 111, the longitudinal section of FIG. 5 being more schematic. In FIG. 5 there may be seen the generally cylindrical exterior surface of the vibration-transmitting fiber 132, the generally cylindrical interior surfaces of the passageways 119 and 119', and in longitudinal section the materials 151, 153 of the catheter 111. In FIG. 6 there appear in cross-section the fiber 132 and the materials 151, 153 of the catheter 111; and as open cavities the lumens 119, 119'.

As suggested in these drawings, the catheter 111 may have a separate sheath 151 and a body material 153 in which the lumens 119 and 119' are formed and the transmitting fiber 132 is embedded. This sheath 151 may be provided as a separate element for certain purposes that will become clear in connection with the later discussion of FIG. 7. Alternatively, the sheath 151 may be provided as a separate element purely for structural reasons, if it is desired to impart strength, slipperiness or other properties to the outer surface that are not desired in the inner body 153. Generally speaking the vibration conducted along the fiber 132 will be sufficiently well confined to the fiber itself—with respect to propagation radially from the wall of the fiber—as to obviate the need for a sheath of the vibration-absorbing type as indicated in FIG. 1.

Hence, if preferred, the catheter may have no separate sheath 151, and the body material 153 may simply be enlarged to encompass the portions shown separately as 151 in FIGS. 5 and 6. In situations incompatible with use of a solid transmitting fiber 132, the fiber may be replaced by a vibration-transmitting liquid sealed in a lumen of the catheter. In this latter case a vibration-absorbing sheath as discussed in connection with FIGS. 2 and 3 may be desirable, or the vibration-transmitting lumen may be disposed more centrally in the catheter body 153 and the body 153 made of vibration-absorbing material.

Also shown in FIG. 6 are other optional lumens 132', defined in the body material 153, that may be used for any number of other purposes such as pressure measurement, insertion of microminiaturized viewing apparatus, and so forth. In some instances the operation of our invention may facilitate these other purposes.

Figure 7:
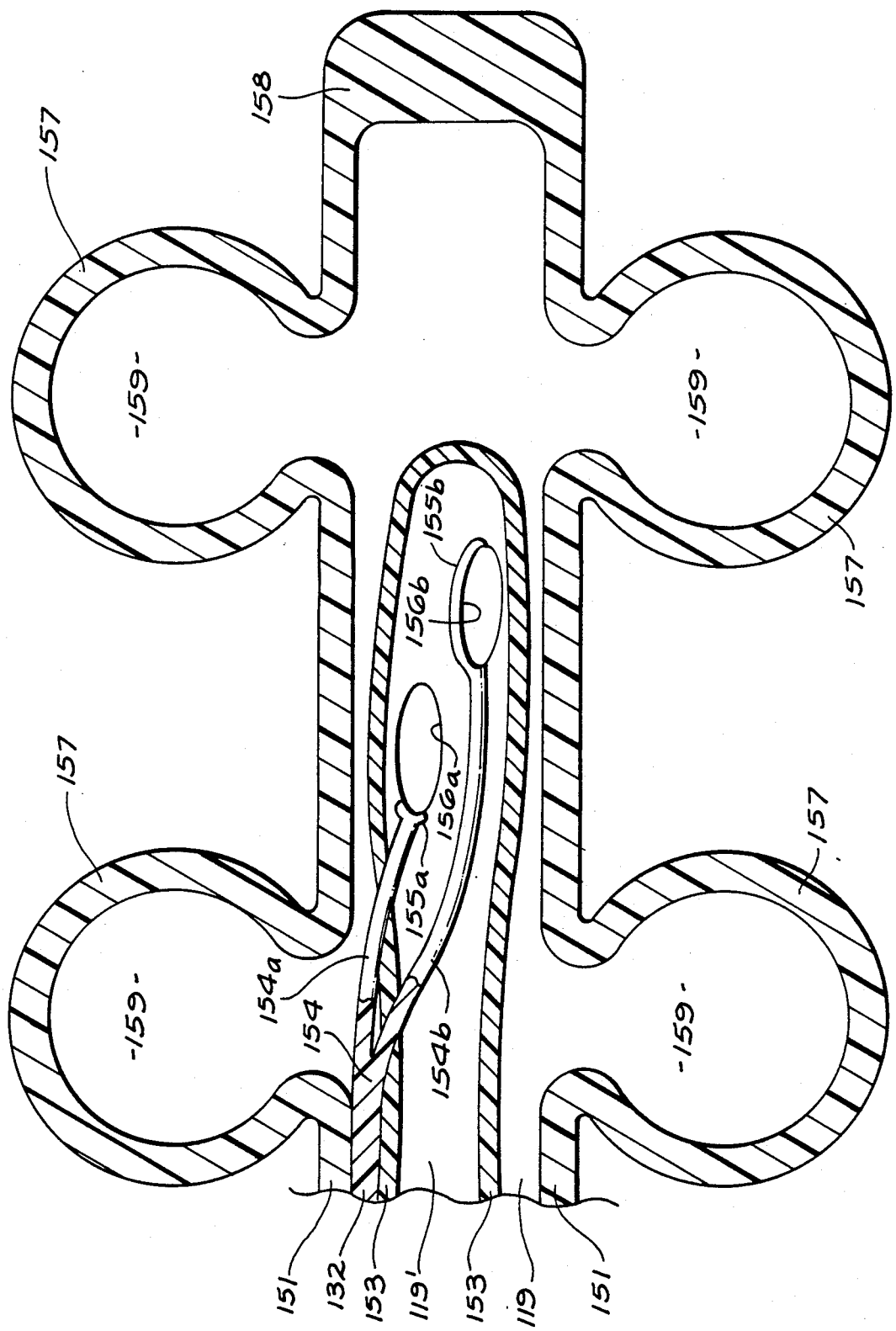
FIG. 7 is an enlarged longitudinal section, analogous to FIG. 5, but taken at the proximal end of the catheter of the FIG. 4 embodiment.

FIG. 7 shows the proximal end of the catheter of FIGS. 4 through 6. As indicated, the outer sheath 151 may be convoluted to form annular gas-diffusion bags or balloons 157. The volume 159 enclosed within these annular bags 157 communicates with the input passageway 119, and the material of the balloons 157 may be semipermeable so as to permit supply of oxygen or other therapeutic gas into a particular region within the patient's body. As before the proximal end of the sheath may be formed, as illustrated, into a somewhat elongated tip 158 for absorption of radially projected vibration (though vibration will typically be confined by the intrinsic operation of the transmitting fiber 132); or may be shaped to facilitate insertion of the catheter.

Within the sheath 151 and the balloons 157, at the proximal end of the catheter, is the inner enclosure 153 that forms the extension of the body material 153 of FIGS. 5 and 6. This inner enclosure 153 is for the purpose of conducting waste fluids away from a site within the patient's body, collecting such waste fluids through orifices 156a and 156b. These orifices may either open into the gas-diffusion balloons, or pass through the outer shield 157 and open directly into the patient's body (or some orifices may do one and some the other) as appropriate to the patient's circumstances and the therapy in use.

In practice there may be multiple orifices, rather than only two as illustrated. The orifices may be oval with the long dimension of each orifice paralleling the axis of the catheter, as illustrated. Instead the orifices may have any number of other shapes or orientations as found appropriate for the particular application and the particular vibrational frequencies, power levels, and propagational modes in use.

The vibration-transmitting fiber 132 is bifurcated as at 154 and its two tips pass into the wall 153 of the inner chamber, and embedded in this wall they proceed directly to terminations 155a and 155b adjacent to the two orifices 156a and 156b respectively. (For simplicity of the drawings the terminations are drawn in solid lines, although it is to be understood that the tips and terminations 155a, 155b are actually embedded in the wall adjacent the orifices 156a, 156b.) In practice the fiber 132 may more likely have multiple endings passing to multiple orifices respectively. If desired the terminations 155a and 155b may be broadened tips, as shown, of the fibers 154a and 154b—to more effectively broadcast the vibrational energy into the entire space defined by each orifice. These tips may be disposed adjacent a short dimension of the periphery of each orifice, as at 155a, or adjacent a long dimension as at 155b, depending upon the frequencies to be used, the types of undesirable substance anticipated, and so forth.

FIG. 8 represents a more highly preferred embodiment of our invention, in which feedback information reflecting the efficacy of the vibrational cleansing is used to optimize that efficacy. Features in FIG. 8 that have reference numerals similar (with the prefix "2") to the numerals in FIGS. 1 through 7 correspond to the features in those earlier drawings. Thus vibration is transmitted along a fiber 232, as suggested by the arrow at 261, through the catheter 211 into the patient's body; while fluids proceed via passageway 219 into the patient's body as indicated by the arrow at 218, and fluids leave the patient's body via passageway 219' as indicated by the arrow at 218'.

In addition, in the FIG. 8 system there is within the catheter 211 a vibration-sensor feedback fiber 272. This feedback fiber 272 carries unabsorbed vibration from the proximal end of the catheter as suggested by the arrows 277 back to the distal end 272, and thence along a similar fiber 272a, 271 to a vibration sensor 273. Here the vibration is advantageously made to generate an electrical signal 278 related to the amplitude of the vibration received at the sensor 273.

The sensor 273 may be any of various forms of vibration sensor. For example, the sensor may include a piezoelectric crystal driving a high-impedance preamplifier or FET electrometer. Such devices may not be fast enough to follow the vibration cycle as such, but they may be able to detect rectified signals from the crystal and thereby provide a measure of vibration amplitude.

Alternatively the sensor 273 may comprise an optical system which geometrically amplifies the mechanical displacement at the distal end of the fiber 271—as by directing a light beam onto the polished fiber tip at an angle and detecting the displacement amplitude of the reflected beam. As another example the sensor 273 may incorporate an interferometric system: a laser beam may be reflected from the fiber tip, and the system made to count the number of resulting optical fringes that pass a photodector per cycle of the mechanical vibration.

In still another system, the distal end of fiber 271 may take the form of a very long coil. A half-silvered, angled surface may be formed along the fiber 271 and used to introduce a laser beam into the coiled portion of the fiber. Phase differences in the laser beam due to the periodic elongation of the fiber coil may be detected at the distal tip of the fiber. It will be understood that these examples are merely exemplary and not intended to be exhaustive.

An electrical signal 278 from the vibration sensor is received in the automatic frequency-control block 275, which produces a frequency-varying feedback signal 281 for passage to the oscillator and amplifier 221, as suggested by the arrow at 282. This signal 281 may simply act to maintain maximum absorption of vibration at the proximal end of the catheter 211. Preferably, however, the automatic frequency control 275 may be programmed to force the vibration frequency to "dwell" at plural or multiple values that correspond to local maxima in the vibration-absorption spectrum of the substances at proximal end of the catheter. Known techniques of electronics and mechanics may be used to change the frequency or amplitude, or to sweep or skip frequencies, or to provide pulses (rather than continuous vibrations) of various frequencies and amplitudes, and so forth.

The automatic frequency control 275 may also be programmed to cause the vibration frequency to dwell at one or more predetermined values that are known to correspond to acoustic resonances within, or wall resonances of, the vibration guard or trap structures 48a, 48b, 48c (FIG. 3). The purpose of this provision is to help keep the guard or trap structures clear. The frequency control 275 may require separate programming for this purpose since, due to the resonance, the feedback system 272-281 may report these frequencies as corresponding to absorption minima.

One convenient form of connector block 262 also appears in FIG. 8. The block has nipples 268 that fit tightly into the passageways 219, 219' at the distal end 272 of the catheter 211. Passageways 269 in the block 262 provide communication between the supply passageway 219 in the catheter 211 and a supply hose 215, and between the drain passageway 219' and a drain hose 215'. The block also has nipples 265 that fit tightly into the lumens of these hoses 215, 215'. Thus the block 262 effectively secures the catheter 211 and hoses 215, 215' together with their corresponding passageways in communication.

In addition the block has apertures 263, 267 for free passage of the vibration-transmitting fibers 232, 272. These apertures may be used as convenient protective locations for lightweight, vibration-transmitting couplings 264, 266 that provide continuity of the cleaning-vibration transmitting fibers 232, 232a and continuity of the feedback-vibration transmitting fibers 272, 272a, respectively.

The transmission fibers either are cemented into their respective couplings 264, 266 or are press-fit or threaded together so that the catheter can be repetitively disconnected from and reconnected to the block 262. For example, the proximal end of the connector 264 and the exposed distal tip of the fiber 232 in the catheter 211 can be threaded together with one handedness of thread, while the distal end of the connector 264 and the proximal tip of the fiber 232a that carries vibration from the horn 225 can be threaded together with the opposite handedness of thread. Thus the connector 264 can be rotated in one direction to screw it onto the tips of both fibers 232 and 232a simultaneously, or rotated in the other direction to unscrew it from both fibers simultaneously.

As shown in FIGS. 9 and 10 the intermediate structure of the catheter is similar to that of FIGS. 5 and 6, with the addition of the vibration-sensor feedback fiber 232'. Like the cleaning-vibration fiber 132 (FIG. 6) or 232', the feedback fiber 232 is embedded within the body material 253 of the catheter.

FIG. 11 shows one of many possible arrangements of the proximal tips 255, 257 of the fibers 254 (232 in the earlier drawings) and 232'. The walls 253 of the lumen 219 appear at the top and bottom of the drawing. An outer sheath or gas-diffusion balloons may also be provided as in FIG. 7, but for simplicity of the drawing they are not shown in FIG. 11. If not required for the application at hand, the outer sheath or balloons may be omitted; thus the drawing in FIG. 11 should be understood to represent either one lumen of a bidirectional catheter or the single lumen of a supply or drain catheter.

As an aid to conceptualizing the operation of this preferred embodiment of our invention, a small accretion of undesirable substance 291 is represented in FIG. 11. It will be understood that in continuous operation of our invention such accumulations will be minimal or nonexistent; however, in certain cases for various therapeutic reasons that may arise the vibration source may not be operated continuously. Hence small deposits 291 may develop while the source is turned off.

Though drawn in solid lines for clarity of the illustration, the cleaning-vibration fiber 254 is embedded in the catheter wall adjacent to a supply or drain orifice 256, as described in connection with FIG. 7. The termination 257 of the feedback fiber 232' is similarly embedded within the catheter wall, diametrically across the supply or drain orifice 256 from the termination 255 of the cleansing-vibration fiber 254. As indicated in connection with FIG. 7, the geometry of the orifice 256 and of the fiber terminations 255 and 257 can vary widely.

Vibration from the input-fiber termination 255 that is not absorbed in disintegration of undesirable substances 291 within the orifice 256 is transmitted across the orifice 256 via liquids within the orifice to the feedback-fiber termination 257. The termination 257 absorbs some of this unused vibrational energy and transmits it back along fiber 232' to the sensor 273, for use as previously described.

The relative configuration of the transmitting and receiving terminations 255 and 257 respectively may take various forms. For example the two terminations may be adjacent one another on a common side of the orifice 256, with a vibration reflector disposed at the opposite side, if such a configuration is found particularly effective. Such a reflection system might be desirable, for example, to generate an absorption measurement that is representative of phenomena just outside the orifice—i.e., just beyond the catheter wall—as well as immediately within the orifice 256.

FIG. 12 illustrates a configuration of transmitting and receiving terminations 455 and 457 that is more specifically designed to be sensitive to measurement of vibration outside the catheter wall. In fact, this configuration is particularly directed to the monitoring of vibration leakage, although it may also be useful under some circumstances to monitor absorption for the purposes discussed above in connection with FIGS. 8 through 11.

The system of FIG. 12 is contemplated for use in generating an alarm signal—or in shutting down or lowering the amplitude of the vibration automatically—if the vibration levels outside the catheter are high enough to pose a threat to the patient's body tissues.

In FIG. 12 the transmitting termination 455 is disposed within the catheter wall. This termination 455 points into the orifice 456, to project vibration toward deposits on the surfaces of the orifice or toward bacteria or large particles suspended in the fluid within the orifice—and even within the lumen 419'. (Under some circumstances it may be preferred to instead position the transmitting termination 455 inside the lumen 419', to better isolate the vibration from the patient's tissues.) The receiving termination 457 is positioned outside the orifice, in the external wall of the catheter, in a region where the vibration level tends to be correlated with the vibration level actually reaching the patient's body tissues.

As will be apparent from the foregoing description, a great amount of variation in the placement and orientation of the receiving termination 457 is possible. That is to say, the termination 457 may be closer to or farther from the orifice 456, or may point toward or away from the orifice, or may point at various angles radially outward from the catheter external surface. The optimum precise positioning and orientation must be determined for each application, taking into account how delicate the particular tissues are, and how close to the catheter tip those tissues are, in the part of the body where the catheter tip will be.

Duration of the expected exposure should also be taken into account in selecting the received vibration amplitude at which the alarm or automatic vibration-control system is triggered.

As will be recalled in connection with FIGS. 1 through 3, liquid being supplied or drained through the catheter of our invention may serve as the conducting medium for conveyance of vibration to the catheter orifices. For various reasons, however, such liquid may be regarded as unsuited to the vibration-transmitting function.

For example, the dynamic properties of a liquid being drained from the patient's body may be found to vary unpredictably with both the concentration and the type of particulate inclusions in the drain liquid. As another example, medicinal or nutritive properties of certain fluids being supplied to the patient's body may deteriorate under the influence of the transmitted vibration. Likewise gaseous fluids in most situations will be unsuited for supporting effective vibrational power transmission.

It is also possible, however, that solid transmitting fibers may be undesirable in some applications. In such cases it may be appropriate to consider the use of nonsolid vibration-conveying means other than the liquid being drained or supplied. FIGS. 13 through 15 illustrate a form of our invention that uses such nonsolid conveying means.

As shown, the catheter used in this embodiment of our invention has a supply or drain lumen 719 for flow of fluids in or out of the patient's body as suggested by the two-headed arrows 717, 718. The catheter also has an auxiliary lumen (or lumens) containing a liquid 732 which is not drained from or supplied into the patient's body tissues or cavities. Rather this liquid 732 is present for the particular purpose of conducting vibration from a converter 723 (FIG. 15) to the regions adjacent the several proximal orifices 756, 756a–756d. Vibration transmission through the fluid 732 is represented by the arrows 761.

The particular auxiliary lumen illustrated in FIGS. 13 through 15 is annular, being formed as a space between an external, generally cylindrical wall 751 and an internal, generally cylindrical wall 753. If preferred the auxiliary lumen (or lumens) need not be annular but may simply parallel the supply or drain lumen 719.

The fluid may be sealed statically within the auxiliary lumen, or if desirable it may be circulated through the auxiliary lumen by dividing the auxiliary lumen into two or more generally longitudinal channels and using one or more of these channels for liquid flow in each direction. (FIGS. 13 through 15 may be interpreted as representing either arrangement, since generally longitudinal dividing walls could be disposed along the catheter out of the plane of the drawings in FIGS. 13 and 15.) Though the liquid in certain channels would be moving in opposite directions, vibration could nevertheless be conducted in the distal-to-proximal direction through the moving fluid in all the channels.

Orifices 756, 756a–756d pass through the annular auxiliary lumen containing the liquid 732, but with respect to fluid communication they are isolated from the annular auxiliary lumen by the orifice walls 755. These walls 755 do, however, receive the vibration 761 through the liquid 732 and serve to transmit this vibration into the orifices 756, 756a–756d. The orifices may be tapered at one end or the other as at 756b and 756d, or they may have outwardly projecting vibration-guard contours (discussed earlier) as at 756c, or both. Alternatively they may be simple cylindrical shapes as at 756a, and so forth.

The form of our invention illustrated in FIGS. 13 through 15 does not necessarily incorporate any vibration-sensor feedback feature. Such a feature, however, is readily provided. For example, the auxiliary lumen may be divided into a number (perhaps ideally an even number) of generally parallel auxiliary lumens by longitudinal walls which intersect the orifice walls 755. Every other auxiliary lumen around the periphery of the annulus may then be used for transmitting vibration to all the orifice walls 755, and the alternate lumens may be used for receiving vibration from the diametrical walls of the same orifices.

The auxiliary lumens may all be straight and essentially parallel to the supply or drain lumen 719, with the orifices therefore all aligned in corresponding straight parallel rows along the outer surface of the catheter. (Once again FIGS. 13 through 15 may be interpreted as illustrating either a system with or without discrete plural lumens.) If preferred, however, and if practical to construct, the auxiliary lumens may spiral or meander in any other pattern, provided only that the orifices are positioned along the walls that separate the plural auxiliary lumens.

The use of plural auxiliary lumens for circulation of the vibration-conducting liquid is compatible with the use of plural auxiliary lumens for provision of a vibration-sensing feedback system. That is, both liquid circulation and vibration-sensing feedback may be provided using the same set of two or more lumens.

Whether solid or liquid vibration-transmitting media be employed, it is not strictly necessary to measure the absorption at every orifice, as long as the number of vibration-sensor feedback paths is sufficient to permit an adequate measurement of typical absorption. Groups of orifices in different regions along the length of the catheter, however, are likely to be subject to accumulation of undesirable substances to differing extents. Furthermore, different substances are likely to accumulate at different regions along the length of the catheter. Hence it is essential to provide for absorption measurements at a number of sites that are sufficiently various to canvass all the principal operating conditions that are anticipated—and thus to identify all the absorption-vs.-frequency maxima necessary to keep the orifices clear in all the different regions.

It will also be understood that different vibration-conductive paths, whether solid or liquid, may be provided for different regions along the length of the catheter, and correspondingly different vibration-sensor feedback paths may likewise be provided. Data acquisition of this discriminating type makes it possible to direct to each group of orifices only vibration at frequencies appropriate to the accretions in those particular orifices. For this purpose the source components mentioned earlier, as well as the vibration sensor feedback system (including the sensor and automatic frequency-control modules) may be time-shared between the separate conductive paths. If desired, however, each set of conductive paths may be provided with its own correspondingly separate source components (oscillator and amplifier, and converter), and a correspondingly separate set of vibration-sensor and automatic frequency-control modules. Using this approach each different group of orifices may receive vibration appropriate to its own accretions continuously, though at increased cost.

The ultrasound waves or other mechanical vibrations may be conducted through liquids, plastics such as nylon, metals or other materials. A preferred conduit is a quartz fiber, one to two millimeters in diameter and of length varying with the length of the tube.

We believe that shear waves are preferred since they can be more effectively controlled at the proximal orifices of a catheter and—due to their rapid attenuation outside the catheter—they should be more effective in breaking up solid material or bacteria at the orifices without injuring adjacent body tissue. The shear waves may be polarized either horizontally or vertically, though we believe that horizontal polarization is preferable to minimize radiation into adjoining tissues of the host. The vibration may be either continuous wave ("CW"), or pulsed or periodic.

Ultrasound and other vibrational frequencies can be varied and easily controlled to "match" the size of certain selected bacteria or other particles. By obtaining such resonances the bacteria can be killed, and bacteria or other particles destroyed, selectively on the basis of mass and shape. This fact has enormous implications for the success of our invention, since it means that the cleansing mechanism can follow the bacteria through at least any imaginable kinds of mutation and structure.

In hospitals and like medical facilities, our invention may be best implemented by providing a centrally located transducer that transmits vibration through fibers to a connector at each bed. Attendants thus would plug each catheter into a vibration-source connector just as they plug other equipment into electrical-source connectors. Alternatively an individual transducer can be used for each individual catheter.

The catheters themselves may be either disposable or reusable.

It is to be understood that all of the foregoing detailed descriptions are by way of example only, and not to be taken as limiting the scope of our invention—which is expressed only in the appended claims.

We claim:

1. A self-cleaning indwelling catheter system for enhanced nonsurgical protracted transfer of fluid between a patient's body and a point outside such patient's body, comprising:
   an indwelling catheter particularly adapted for such nonsurgical protracted transfer of fluid between such patient's body and a point outside such patient's body;
   at least one orifice that is defined near the proximal end of the catheter and that is subject to the presence of undesirable substance within the orifice or on the catheter at the orifice, or both, during such nonsurgical protracted transfer of fluid;
   a source of mechanical disintegrating vibration; and
   means for conveying the disintegrating vibration from the source to the orifice and concentrating the disintegrating vibration at the orifice to disintegrate the undesirable substance and so maintain such nonsurgical protracted transfer of fluid relatively free from obstruction and contamination by the undesirable substance;
   whereby the source and conveying means cooperate to prevent blockage of, or infection at, said catheter, or both, and to facilitate and enhance the nonsurgical protracted fluid-transfer purpose of the indwelling catheter.

2. The catheter system of claim 1:
   wherein said source of vibration supplies said vibration, substantially continuously or pulsed, for at least prolonged time periods during such protracted transfer of fluid; and
   further comprising means, disposed adjacent to the orifice, for deterring propagation of the vibration into the parts of the patient's body outside the catheter to avoid injury to those parts during the prolonged time periods.

3. The catheter system of claim 1, wherein:
   the catheter has a lateral wall;
   the orifice is defined in the lateral wall; and
   the vibration-conveying means comprise a solid fiber in the catheter, adapted and disposed to conduct the vibration directly to the orifice.

4. The catheter system of claim 1, wherein:
   the vibration is at least primarily at ultrasonic frequencies.

5. The catheter system of claim 1, further comprising:
   a vibration-absorbing tip fixed at the proximal end of the catheter, to deter propagation of the vibration into the parts of the patient's body beyond the proximal end of the catheter.

6. The catheter system of claim 1, further comprising:
   a vibration-absorbing raised guard rim surrouding the orfice, to deter propagation of the vibration into the parts of the patient's body outside the catheter.

7. The catheter system of claim 6, wherein:
   the orifice has an axis; and
   the guard rim is spaced radially, relative to the axis of the orifice, outward.

8. A self-cleaning catheter system, for use in protracted transfer of fluid between a patient's body and a point outside such patient's body, comprising:
   a catheter that has a wall and is adapted for such protracted transfer of fluid;

at least one orifice that is defined near the proximal end of the catheter and that is subject to the presence of undesirable substance during such transfer of fluid;

a source of mechanical vibration; and means for conveying the vibration from the source to the orifice to disintegrate the undesirable substance and maintain such protracted transfer of fluid relatively free from obstruction and contamination by the undesirable substance, the vibration-conveying means comprising a solid fiber embedded in the wall of the catheter, and adapted and disposed to conduct the vibration directly to the orifice.

9. A self-cleaning catheter system, for use in protracted transfer of fluid between a patient's body and a point outside such patient's body, comprising:

a catheter that is adapted for such protracted transfer of fluid and that defines two lumens, one for such transfer of fluid and the second for containing a vibration-conducting liquid;

at least one orifice that is defined near the proximal end of the catheter and that is subject to the presence of undesirable substance during such transfer of fluid;

a source of mechanical vibration; and means for conveying the vibration from the source to the orifice to disintegrate the undesirable substance and maintain such protracted transfer of fluid relatively free from obstruction and contamination by the undesirable substance, the vibration-conveying means comprising a liquid constrained within the second lumen, adapted and disposed to conduct the mechanical vibration directly to the orifice; and the catheter further comprises structure preventing fluid communication between the second lumen and the orifice.

10. The catheter system of claim 9, wherein:

the catheter has a double wall, comprising two walls one within the other;

the first lumen is defined within the inner wall;

the second lumen is an annular space defined between the two walls of the catheter;

the orifice passes through the double wall; and the structure comprises an orifce wall that prevents fluid communication between the annular space and the orifice.

11. A self-cleaning indwelling-catheter system, for use in protracted transfer of fluid between a patient's body and a point outside such patient's body, comprising:

an indwelling catheter adapted for such protracted transfer of fluid between such patient's body and a point outside such patient's body;

at least one orifice that is defined near the proximal end of the catheter and that is subject to the presence of undesirable substance within the orifice or on the catheter at the orifice, or both, during such transfer of fluid;

a source of mechanical disintegrating vibration;

means for conveying the disintegrating vibration from the source to the orifice and concentrating the disintegrating vibration at the oriface to disintegrate the undesirable substance and maintain such protracted transfer of fluid relatively free from obstruction and contamination by the undesirable substance; and means for measuring the absorption of the vibration by such substance;

said measuring means including apparatus disposed outside such person's body and connected to be responsive to vibrational energy not absorbed by such substance.

12. The catheter system of claim 11, further comprising:

means for adjusting the frequency or amplitude of the vibration;

said adjusting means including apparatus disposed outside such person's body and connected to control the vibration source.

13. The catheter system of claim 12, wherein:

the adjusting means are automatically responsive to the measuring means to adjust the frequency or amplitude of the vibration to maximize the absorption of the vibration by such substance.

14. The catheter system of claim 12, wherein:

the adjusting means are automatically responsive to the measuring means to select a plurality of frequencies having relatively high values of absorption and adjust each frquency, or the amplitude of the vibration at each frequency, of the plurality to maximize the absorption of the vibrational energy by such substance.

15. A self-cleaning catheter system, for use in protracted transfer of fluid between a patient's body and a point outside such patient's body, comprising:

a catheter adapted for such protracted transfer of fluid;

at least one orifice that is defined near the proximal end of the catheter and that is subject to the presence of undesirable substance during such transfer of fluid;

a source of mechanical vibration;

means for conveying the vibration from the source to the orifice to disintegrate the undesirable substance and maintain such protracted transfer of fluid relatively free from obstruction and contamination by the undesirable substance, the vibration-conveying means comprising a solid fiber in the catheter, adapted and disposed to conduct the vibration directly to the orifice;

means for measuring the absorption of the vibration by such substance, including a second solid fiber adapted and disposed to transmit vibration that is not absorbed by the substance back through the catheter and out of such patient's body; and means for adjusting the frequency or amplitude of vibration.

16. The catheter system of claim 15, wherein:

the adjusting means are automatically responsive to the measuring means to adjust the frequency or amplitude of the vibration to maximize absorption.

17. The catheter system of claim 15, wherein:

the adjusting means are automatically responsive to the measuring means to select a plurality of frequencies having relatively high values of absorption and adjust each frequency, or the amplitude of vibration at each frequency, of the plurality to maximize the absorption of the vibration by such substance.

18. A self-cleaning indwelling-catheter system, for use in protracted transfer of fluid between a patient's body and a point outside such patient's body, comprising:

an indwelling catheter adapted for such protracted transfer of fluid between such patient's body and a point outside such patient's body;

at least one orifice that is defined near the proximal end of the catheter and that is subject to the presence of undesirable substance within the orifice or on the catheter at the orifice, or both, during such transfer of fluid;

a source of mechanical disintegrating vibration; and means for conveying the disintegrating vibration from the source to the orifice and concentrating the disintegrating vibration at the orifice to disintegrate the undesirable substance and maintain such protracted transfer of fluid relatively free from obstruction and contamination by the undesirable substance;

wherein the source and the conveying means cooperate to provide such vibration at the orifice in the form of shear waves;

whereby such vibration is effectively controlled at the proximal orifice and is effective in disintegrating the substance, to prevent blockage of such indwelling catheter or infection at such indwelling catheter, or both, without injuring adjacent body tissue.

19. A self-cleaning indwelling-catheter system, for use in protracted transfer of fluid between a patient's body and a point outside such patient's body, comprising:

an indwelling catheter adapted for such protracted transfer of fluid between such patient's body and a point outside such patient's body;

at least one orifice that is defined near the proximal end of the catheter and that is subject to the presence of undesirable substance within the orifice or of the catheter at the orifice, or both, during such transfer of fluid;

a source of mechanical disintegrating vibration;

means for conveying the disintegrating vibration from the source to the orifice and concentrating the disintegrating vibration at the orifice to disintegrate the undesirable substance and maintain such protracted transfer of fluid relatively free from obstruction and contamination by the undesirable substance; and means for measuring the leakage of vibration away from the catheter toward such patient's body tissues;

said measuring means including apparatus disposed outside such person's body and connected to be responsive to vibrational energy not absorbed by such substance.

20. The catheter system of claim 19, further comprising:

means, responsive to the measuring means, for triggering an alarm if the leakage exceeds a threshold value.

21. The catheter system of claim 19, further comprising:

means, responsive to the measuring means, for reducing the vibration amplitude if the leakage exceeds a threshold value.

22. The catheter system of claim 19, further comprising:

means, responsive to the measuring means, for adjusting the vibration amplitude to prevent the leakage form exceeding a predetermined permissible amount.

23. A self-cleaning indwelling-catheter system, for use in protracted transfer of fluid between a patient's body and a point outside such patient's body, comprising:

an indwelling catheter adapted for such protracted transfer of fluid between such patient's body and a point outside such patient's body;

at least one orifice that is defined near the proximal end of the catheter and that is subject to the presence of undesirable substance within the orifice or on the catheter at the orifice, or both, during such transfer of fluid;

a source of mechanical disintegrating vibration; and means for conveying the disintegrating vibration from the source to the orifice and concentrating the disintegrating vibration at the orifice to disintegrate the undesirable substance and maintain such protracted transfer of fluid relatively free from obstruction and contamination by the undesirable substance; and wherein:

the cahteter has a wall;

a vibration-absorbing raised guard rim on the wall surrounds the orifice and is spaced radially, relative to the axis of the orifice, outward;

a flange is formed on the guard rim projecting radially, relative to the axis of the orifice, inward; and a secondary aperture, generally coaxial with but spaced from the orifice, is defined by the radially innermost surface of the flange; and the rim, flange and secondary aperture form with the wall a disc-shaped trap chamber to deter propagation of the vibration into the parts of the patient's body outside the catheter.

24. The catheter system of claim 23, wherein:

the catheter has outside the wall an outer sheath of vibration-absorbing material, said orifice penetrating both the wall and the sheath; and the rim and flange are formed on the sheath.

25. The catheter system of claim 23, wherein:

the vibration has a nominal center frequency; and the trap chamber is sized to resonate at the nominal center frequency.

* * * * *